(12) United States Patent
Bhardwaj et al.

(10) Patent No.: US 7,579,437 B2
(45) Date of Patent: Aug. 25, 2009

(54) POLYPEPTIDES AND METHODS FOR MAKING THE SAME

(75) Inventors: Ranjit Bhardwaj, Berlin (DE); Birgit Vogt, Berlin (DE); Ahmed Sheriff, Berlin (DE)

(73) Assignee: TheraVision GmbH, Berlin (DE)

( * ) Notice: Subject to any disclaimer, the term of this patent is extended or adjusted under 35 U.S.C. 154(b) by 0 days.

(21) Appl. No.: 10/547,364

(22) PCT Filed: Feb. 27, 2004

(86) PCT No.: PCT/EP2004/001986

§ 371 (c)(1),
(2), (4) Date: Jun. 9, 2006

(87) PCT Pub. No.: WO2004/076479

PCT Pub. Date: Sep. 10, 2004

(65) Prior Publication Data

US 2006/0264613 A1    Nov. 23, 2006

(30) Foreign Application Priority Data

Feb. 27, 2003  (EP)  .................. 03004445

(51) Int. Cl.
*C07K 14/00* (2006.01)
*A61K 38/16* (2006.01)

(52) U.S. Cl. ........................ 530/350; 514/12
(58) Field of Classification Search ............ None
See application file for complete search history.

(56) References Cited

U.S. PATENT DOCUMENTS

| | | | |
|---|---|---|---|
| 5,851,795 A * | 12/1998 | Linsley et al. | 435/69.1 |
| 5,885,796 A | 3/1999 | Linsley et al. | |
| 6,812,339 B1 * | 11/2004 | Venter et al. | 536/24.31 |
| 6,875,904 B2 * | 4/2005 | Liu et al. | 800/18 |

FOREIGN PATENT DOCUMENTS

| | | |
|---|---|---|
| WO | WO 95/01994 | 1/1995 |
| WO | WO 97/47732 | 12/1997 |

OTHER PUBLICATIONS

Attwood T., Science 2000; 290:471-473.*
Skolnick et al., Trends in Biotech. 2000; 18(1):34-39.*
Metzler et al., Nature Structural Biol. 1997; 4:527-531.*

\* cited by examiner

*Primary Examiner*—Ilia Ouspenski
(74) *Attorney, Agent, or Firm*—Jacobson Holman PLLC

(57) ABSTRACT

An isolated protein having at least 90% homology with the dimeric protein having the following amino acid sequence (I) with the proviso that at the C-terminal end of the monomeric forms, 2 to 10 amino acid distance from $Z^2$, a Cys is present for forming the dimeric or multimeric protein, $Z^1$ is a signal peptide for protein transport to the ER and/or through the plasma membrane or $NH_2$ or a derivative of an $NH_2$ group such as an alkylated, or acylated derivative, or polyethylene glycol (PEG) moiety, $Z^2$ is an amino acid residue with up to 20, in particular 10 or 8 amino acids which are selected of substantially non-hydrophobic naturally occurring amino acids or $COOZ^3$ wherein $Z^3$ is hydrogen, a metal ion, a hydrocarbon moiety substituted or non-substituted with heteroatoms.

(I)

$Z^1$mhvaqpavvlassrgiasfvceyaspgkatevrvtvlrqadsqvtevcaatymtgneltflddsic⎤
                                                                      |
tgtssgnqvnltiqglramdtglyickvelmypppyylgigngtqiyvidpepcpds-$Z^2$
                                                                      |
gtssgnqvnltiqglramdtglyickvelmypppyylgigngtqiyvidpepcpds-$Z^2$
                                                                      |
$Z^1$mhvaqpavvlassrgiasfvceyaspgkatevrvtvlrqadsqvtevcaatymtgneltflddsict

10 Claims, No Drawings

SEQUENCE LISTING

<160> NUMBER OF SEQ ID NOS: 2

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence:monomeric
      recombinant CTLA4 polypeptide

<400> SEQUENCE: 1

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Thr Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
           100                 105                 110

Tyr Val Ile Asp Pro Glu Pro Cys Pro Asp Ser
        115                 120

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence:monomeric
      recombinant CTLA4 polypeptide

<400> SEQUENCE: 2

Met Ala Cys Leu Gly Phe Gln Arg His Lys Ala Gln Leu Asn Leu Ala
 1               5                  10                  15

Ala Arg Thr Trp Pro Cys Thr Leu Leu Phe Phe Leu Leu Phe Ile Pro
            20                  25                  30

Val Phe Cys Lys Ala
        35

POLYPEPTIDES AND METHODS FOR MAKING THE SAME

This is a 371 of PCT/EP2004/001986 filed 27 Feb. 2004.

The present invention relates to soluble proteins useful for controlling T cell activation, and more particularly to soluble CTLA4 proteins produced by recombinant DNA methods.

BACKGROUND OF THE INVENTION

Inappropriate T cell activation has been implicated in a number of deleterious conditions, including autoimmune diseases and transplant rejection. Optimal activation of T cells for clonal expansion is believed to require two signals. One is an antigen-specific signal delivered through T cell receptors (TCR), while the second is an antigen-non-specific or co-stimulatory signal.

The second non-specific signal is determined by a class of T cell regulatory molecules known as co-stimulators that determine whether T cells are activated or not. B7 (1 and 2), are co-stimulatory proteins expressed on the cell surface of antigen presenting cells such as macrophages, B lymphocytes and dendritic cells as reported.

B7 (1 and 2) is a natural ligand for T cell surface proteins known as CD28 and CTLA4 (cytolytic T-lymphocyte-associated antigen number 4, CD152). CD28 and CTLA4 share substantial homology in their amino acid sequences, particularly in the transmembrane and cytoplasmic domains, and are therefore believed to share similar functions in the T-cell co-stimulation pathway. B7 is known to have a greater affinity for CTLA4 compared with CD28.

CD28 is constitutively expressed on most T lymphocytes. CTLA4, however, was determined to be preferentially expressed by activated versus unactivated T cells.

The interactions of B7 with CD28 and CTLA4 play an important role in the full activation of T cells in the co-stimulation pathway during an immune response. Neutralisation of B7 or CD28 activity, for example with monoclonal antibodies, prevents T cell proliferation. Neutralisation of B7 activity also prevents T cells from acting as helper cells for the induction of antibody synthesis by B cells.

However, previous attempts to express the extracellular domain of CTLA4 as a soluble, unfused protein have been unsuccessful. According to PCT Publication No. WO 93/00431, successful expression of active CTLA4 proteins is believed to require an expression system that permits the proteins to form as dimers because the proteins are believed to occur in nature as dimers. Thus, researchers have focused on fusion proteins in an effort to find an appropriate expression system.

A fusion protein containing the extracellular domain of CTLA4 joined to the Fc heavy chain region of an immunoglobulin molecule has been developed as a possible agent having B7 inhibitory activity. This fusion protein, referred to as "CTLA4 Ig fusion protein," is described in Linsley et al., J. Exp. Med. 174:561-569 (1991) and in PCT Patent Publication No. WO-A-93/00431.

According to these publications, the CTLA4-Ig fusion protein is secreted from mammalian cells as a disulfide-linked dimeric protein that aggregates in solution. However, attempts to express the extracellular domain of CTLA4 as an unfused protein in mammalian cells were unsuccessful. The Ig portion of the fusion protein facilitates the formation of a dimeric fusion protein, which is capable of being processed and expressed by the mammalian cells. The Ig portion additionally allows the active fusion protein to be purified from conditioned media using a protein A affinity column. Protein A has a high affinity for the Fc region of Ig molecules.

The molecular weight of the major CTLA4-Ig species in solution is approximately 200 kDa based on size exclusion chromatography also described in Linsley et al., J. Exp. Med. 174:561-569 (1991). Because the molecular weight of the monomeric form of the CTLA4-Ig fusion protein expressed in mammalian cells is about 50 kDa, the major species in solution is believed to be an aggregated complex of at least four CTLA4-Ig molecules.

The B7 inhibitory activity of the CTLA4-Ig fusion protein has been tested in both in vitro and in vivo experiments. In the in vitro experiments, the CTLA4-Ig fusion protein bound to B7 and neutralised its activity. The CTLA4-Ig fusion protein was found to inhibit T cell proliferation. The fusion protein also inhibited the ability of helper T cells to stimulate antibody production by B lymphocytes in an in vitro study described in Linsley et al., J. Exp. Med. 174:561-569 (1991).

In experiments conducted in vivo, the CTLA4-Ig fusion protein was determined to be immunosuppressive and capable of prolonging survival of pancreatic and heart allografts in mice and rats. In mouse studies, the administration of CTLA4-Ig resulted in the long term acceptance of allografts. These results suggest that the fusion protein had tolerized the recipient mice to the foreign tissue.

The CTLA4-Ig fusion protein has several disadvantages as a therapeutic agent for human disease. Because the fusion protein is a non-naturally occurring molecule, a patient receiving the protein may develop an immune response to the protein.

Antigenicity may be more of a problem when patients are taken off the therapeutic agent so they are no longer immunosuppressed and are capable of mounting an immune response against the fusion protein. Therefore, antigenicity may prevent the CTLA-Ig fusion protein from being administered intermittently to patients suffering from chronic diseases. In addition, the half-life of the CTLA4-Ig fusion protein in mice is about 4 days, with significant levels of the fusion protein still detectable in the animals 5 weeks after the cessation of treatment with CTLA4-Ig. Furthermore, when bound to B7 on the surface of antigen-presenting cells, the Ig portion of the fusion protein may activate the complement cascade that results In cell death and hematological problems.

Thus, a need exists for additional therapeutic agents capable of inhibiting the co-stimulatory pathway in T cell activation. The present invention satisfies this need and provides related advantages as well.

SUMMARY OF THE INVENTION

The present invention relates to recombinantly-produced CTLA4 polypeptides that are not fusion proteins containing human Ig molecules. The soluble, recombinant polypeptides contain, as a basic unit, a monomer consisting essentially of the extracellular domain of the CTLA4 receptor protein. Preferably, the recombinant polypeptides are the product of joining two or more monomers through intermolecular sulfide bonds to form biologically active dimers or multimers.

The polypeptides can also be functional derivatives of the monomers and multimers, such as, for example, pegylated molecules.

The present invention also provides methods of making the recombinant polypeptides. The methods include the steps of:

(a) obtaining a DNA sequence capable of directing a host cell to express a polypeptide corresponding to the extracellular domain of a CTLA4 receptor protein, the polypeptide having B7 binding activity;

(b) inserting the DNA sequence into a vector having operational elements for expression of the DNA sequence;

(c) transferring the vector into a host cell capable of expressing the polypeptide;

(d) culturing the host cell under conditions for expression of the polypeptide;

(e) harvesting the active polypeptide.

Vectors and host cells useful for the expression of the recombinant CTLA4 polypeptides are also provided. In addition, the invention further provides pharmaceutical compositions containing the CTLA4 polypeptides as the active ingredient.

The invention is related with an isolated protein having at least 90% homology with the dimeric or multimeric protein having the following amino acid sequence wherein the dimer has the following structures:

$Z^1$mhvaqpavvlassrgiasfvceyaspgkatevrvtvlrqadsqvtevcaatymtgneltflddsic tgtssgnqvnltiqglramdtglyickvelmypppyylgigngtqiyvidpepcpds-$Z^2$ gtssgnqvnltiqglramdtglyickvelmypppyylgigngtqiyvidpepcpds-$Z^2$ $Z^1$mhvaqpavvlassrgiasfvceyaspgkatevrvtvlrqadsqvtevcaatymtgneltflddsict with the proviso that at the C-terminal end of the monomeric forms, 2 to 10 amino acid distance from $Z^2$, a Cys is present for forming the dimeric or multimeric protein.

$Z^1$ is a signal peptide for protein transport to the ER and/or through the plasma membrane or $NH_2$ or a derivative of an $NH_2$ group such as an alkylated, or acylated derivative, or polyethylene glycol (PEG) moiety, $Z^2$ is an amino acid residue with up to 20, in particular 10 or 8 amino acids which are selected of substantially non-hydrophobic naturally occurring amino acids or $COOZ^3$ wherein $Z^3$ is hydrogen, a metal ion, a hydrocarbon moiety substituted or non-substituted with heteroatoms. The monomeric forms may be linked by Cys-Cys bonds or e.g. crosslinked PEG moieties to form di- or multimeric forms. The protein of the invention may be altered by exchange of amino acids as long as the protein is still functional. In most cases this is the case when 90% homology is maintained. The modification of the amino acid chain may be achieved by replacing single amino acids or clusters of amino acids of the sequence or deletions. An exchange of amino acid can in one way be done by a conservative exchange of for example an aromatic amino acid against another aromatic amino acid or by exchange of a cationic amino adds. The $Z^2$ substituent should not be too non-polar in order to avoid a lipophilic area which may cause binding of the protein in membranes.

Subject matter of the invention is also the monomeric part of the dimeric protein of the invention having the following amino acid sequence:

(SEQ ID NO: 1)
$Z^1$mhvaqpavvlassrgiasfvceyaspgkatevrvtvlrqadsqvtevc aatymtgneltflddsictgtssgnqvnltiqglramdtglyickvelmy pppyylgigngtqiyvidpepcpds-$Z^2$ wherein $Z^1$ and $Z^2$ have the same meaning as mentioned above.

The monomer is important since this is coded by a nucleic acid in the cell. The expression of the respective gene leads after post translational modification by the cell to the protein of the invention. Multimeric forms can be formed, starting from this monomer.

A particular signal peptide of the protein of the invention comprises a $Z^1$ residue of the following sequence:

(SEQ ID NO: 2)
maclgfqrhk aqlnlaartw pctllffllf ipvfcka.

In a particular embodiment of the invention the protein of the invention is soluble under physiological conditions.

(SEQ ID NO: 3)

In another embodiment the protein of the invention wherein comprises an extra cellular domain of the CTLA4 protein.

The protein of the invention can bind B7-1 or B7-2.

An isolated nucleic acid coding for the monomeric protein of the invention is also subject matter of the invention. The expression of the respective gene leads after post translational modification by the cell to the protein of the invention.

The expression of the gene in a bacterial or eukaryotic host cell leads to the monomeric protein which dimerises in the cellular medium. When secreted the signal peptide is removed. The nucleic acid may contain a nucleotide sequence encoding a CTLA4 extracellular domain.

A recombinant expression vector comprising a nucleic acid is also subject of the invention. The vector can be used for transfection of a host cell directing the expression of the protein of the invention or directing the expression of a CTLA4 extracellular domain.

The protein of the invention can be formulated in a composition suitable for pharmaceutical administration. The pharmaceutical formulation comprises a protein of the invention, and a pharmaceutically acceptable carrier.

According to the invention the protein of the invention can be produced by a method comprising culturing a host cell of the invention in a medium to express the protein and isolating the protein from the medium or purifying the protein from inclusion bodies.

In another embodiment the inventions concerns a method for producing a fusion protein consisting of a protein of the invention with an immunoglobulin protein comprising culturing a host cell of the invention in a medium to express the protein and purifying the protein by release from periplasm.

The invention claims also a method for inhibiting an interaction of a CTLA4 ligand on an antigen presenting cell with a receptor for the CTLA4 ligand on a T cell the method comprising contacting the antigen presenting cell with a protein of the invention, a method for treating an autoimmune disease in a subject mediated by interaction of a CTLA4 ligand on an antigen presenting cell with a receptor for the CTLA4 ligand on a T cell, comprising administering to the subject the protein of the invention.

In particular the invention is concerned with a method, wherein the autoimmune disease is selected from the group consisting of diabetes mellitus, rheumatoid arthritis, multiple sclerosis, myasthenia gravis, systemic lupus erythematosis, psoriasis vulgaris, myasthenia gravis, Graves' disease, Goodpastures' disease, idiopathic thrombocytopenia purpura (ITP), aplastic anemia, inflammatory bile disease, idiopathic dilated cardiomyopathy (IDM) and autoimmune thyroiditis.

In a further embodiment of the invention the method for treating allergy in a subject is mediated by interaction of a CTLA4 ligand on an antigen presenting cell with a receptor for the CTLA4 ligand on a T cell, comprising administering the protein of the invention to the subject.

In another embodiment a method is disclosed for inhibiting graft-versus-host disease (GVHD) in a bone marrow transplant recipient, comprising administering to the recipient the protein of the invention.

In yet another embodiment a method is disclosed, wherein donor bone marrow is contacted with the protein of any one of the claims 1 to 6 and with cells from the transplant recipient ex vivo prior to transplantation of the donor bone marrow into the recipient.

In still another embodiment antigen presenting cells of the recipient is contacted with the protein of any one of the claims 1 to 6 and with cells, most preferably T cells from the donor.

Another embodiment is concerned with a method for inhibiting rejection of transplanted cells in a transplant recipient, comprising administering to the recipient the protein of the invention.

DETAILED DESCRIPTION OF THE INVENTION

The present invention provides soluble proteins of the CTLA4 type, e.g. recombinantly produced, that are not fused to human Ig molecules protein of the present invention is useful for inhibiting inappropriate T cell activation that can lead to various disorders.

The naturally-occurring or wild-type CTLA4 protein is a ligand of B7, which is a cell surface protein involved in the costimulatory pathway leading to T cell activation. The nucleotide and amino acid sequences of murine and human CTLA4 are reported Brunet, J. F., Denizot, F., Luciani, M. F., Roux-Dosseto, M., Suzan, M., et al. 1987. A new member of the immunoglobulin superfamily—CTLA-4. *Nature* 328:267-70. Dariavach, P., Mattei, M. G., Golstein, P., Lefranc, M. P. 1988. Human Ig superfamily CTLA-4 gene: chromosomal localization and identity of protein sequence between murine and human CTLA-4 cytoplasmic domains. *Eur J Immunol* 18:1901-5. The overall amino acid homology between human and murine CTLA4 proteins is 76%. The correct amino acid sequence of the full length human CTLA4 protein Is provided in PCT Publication No. WO-A-93/00431.

As noted previously, earlier attempts to produce an unfused or truncated CTLA4 protein have been unsuccessful. Therefore, prior to the present invention, methods for obtaining a biologically active, recombinant CTLA4 protein involved expressing CTLA4 as a fusion protein. More particularly, the fusion protein is described in PCT Publication No. WO-A-93/00431 as containing the extracellular domain of CTLA4 fused to the heavy chain region of a human immunoglobulin molecule (referred to as "CTLA4-Ig" protein). According to this publication, successful expression of the extracellular domain of the CTLA4 receptor protein requires an expression system that permits the protein to form dimers. In contrast, the unfused or truncated versions of the CTLA4 protein appeared not to be expressed in an active form in eukaryotes. In contrast, the protein of the invention, however, is an active truncated version of the CTLA4 protein can be produced in eukaryotes. The publication further indicates that the Ig portion of the CTLA4-Ig fusion protein is believed to facilitate dimer formation and to aid in the purification of the fusion protein by conventional protein A affinity chromatography.

The present invention is based on methods for producing biologically active, soluble proteins of the CTLA4-type (sCTLA4) that are not fused to an Ig chain. As used herein, the term "biologically active" refers to polypeptides that exhibit B7 binding activity.

The protein of the invention has, as a basic unit, a monomer that consists essentially of the extracellular domain of the wild-type CTLA4 receptor protein, preferably including the cysteine close to the transmembrane domain. In reference to monomers, the term "consists essentially of" as used herein is intended to encompass a monomer encoded by an amino acid sequence corresponding to the extracellular domain of the wild-type CTLA4 protein or corresponding to the extracellular domain joined to additional amino acids other than an amino acid sequence encoding for a complete human Ig molecule.

The protein of the present invention can also be in the form of dimers or other multimers, which contain more than one basic monomeric unit. Such multimers, particularly dimers, can be formed by joining two or more monomers through intermolecular disulfide bonds or by crosslinking agents such as, for example, polyethylene glycol (hereinafter referred to as "PEG"), other polyethers, EDTA and other linkers known to those skilled in the art.

The present invention further provides methods of producing the protein of the present invention. Such methods include the steps of:

(a) obtaining a DNA sequence capable of directing a host cell to express a polypeptide corresponding to the extracellular domain of a CTLA4 receptor protein, the polypeptide having B7 binding activity;

(b) inserting the DNA sequence into a vector having operational elements for expression of the DNA sequence;

(c) transferring the vector into a host cell capable of expressing the polypeptide;

(d) culturing the host cell under conditions for expression of the polypeptide.

Optionally, the peptide can thereafter be permitted to assume a quaternary structure in which two or more monomers join to form a unit, such as a dimer or other multimeric forms. In addition, the present invention further optionally includes separating the dimeric forms to obtain the form with the most inhibitory activity, referred to herein as the active dimeric form.

As used herein, the term "functional equivalent(s)" means modified sequences having one or more additions, deletions, or substitutions to the above sequence that do not substantially affect the ability of the sequence to encode a polypeptide having B7 binding activity. Such modified sequences can be produced by means known in the art, including, for example, site directed mutagenesis. The sequences can be obtained from natural sources, such as the natural DNA sequence encoding the extracellular domain of a CTLA4 receptor protein. Alternatively, the sequence can be produced synthetically according to methods known in the art. Additionally, such DNA sequences can be derived from a combination of synthetic and natural sources. The natural sequences further include cDNA and genomic DNA segments. Methods of obtaining the synthetic and natural DNA sequences are described in PCT Publication No. WO-A-93/00431, which is incorporated herein by reference.

Vectors that can be used in these methods include those vectors into which a CTLA4 DNA sequence has been introduced, as described above. As used herein, the term "consisting essentially of" In reference to vectors means that such vectors contain nucleotide sequences that encode for the extracellular domain of CTLA4 receptor protein, including any desired operational elements, but not nucleotide sequences encoding a human Ig molecule. A CTLA4 DNA sequence can be inserted and linked with any desired operational elements to effect its expression. The vectors can contain one or more of the following operational elements: (1) a promoter; (2) a Shine Dalgarno sequence and initiator codon; (3) a terminator codon; (4) an operator; (5) a leader sequence to facilitate transportation out of the host cell; (6) a gene for a regulator protein; and (7) any other DNA sequences necessary or preferred for appropriate transcription and subsequent translation of the vectors.

The vectors can be transferred into suitable host cells by various methods known in the art, including transfection and transformation procedures. Various transfer methods are described in Sambrook et al., Molecular Cloning: A Laboratory Manual, Cold Spring Harbor, N.Y. (2000), which is incorporated herein by reference. Such host cells can be either eucaryotic or procaryotic cells. Examples of such host cells include chinese hamster ovary (CHO) cells, Vero cells, HEK293 cells, yeast, *E. coli* and baculovirus infected insect cells.

The host cells of the present invention can be cultured under conditions appropriate for the expression of the protein of the invention. These conditions are generally specific for the host cell and are readily determined by one of ordinary skill in the art In light of the published literature regarding the growth conditions for such cells.

In one embodiment, cells can be grown to a high density in the presence of appropriate regulatory conditions that inhibit expression of the desired protein of the invention. When optimal cell density is reached, the environmental conditions can be altered to those appropriate for expression of the polypeptide according to procedures known in the art or as described in the examples below. Therefore, prior to harvesting the expressed protein of the invention, it is particularly useful to allow the host cells to grow near optimal density before inducing expression.

Expression of the protein of the invention can be confirmed by using anti-CTLA4 antibodies according to assay procedures known in the art, such as Western blotting or ELISA for example. Once expression of the recombinant polypeptides has been confirmed, the polypeptides can then be harvested according to methods known to those skilled in the art.

The recombinant polypeptides can be purified after harvesting.

The present invention also provides functional derivatives of the protein of the invention. As used herein, the term "functional derivative" means any biologically active modified form of the protein of the invention. Such modifications can be (1) substitutions or additions in the amino acid sequence, and/or (2) the addition of another functional group to improve certain pharmacokinetic or immunologic properties. Such modifications, however, should not substantially decrease the biological activity of the parent recombinant polypeptide by no more than a 10-fold decrease, preferably less than a 5-fold decrease in activity. Therefore, as used herein, the term "functional derivative" can mean an active fragment, an analog or a derivative of the protein of the invention described above that substantially retains the biological activity of the unmodified protein of the invention. In the case of analogs, such modified polypeptides preferable have an amino acid homology of greater than about 40% compared to the extracellular domain of CTLA4, more preferably in excess of 50%, and most preferably in excess of 90%. An amino acid homology of about 99% is particularly useful.

For example, one modification can be the substitution or addition of a cysteine to provide a "free cysteine" within the amino acid sequence to produce a "cysteine mutein." The terms "cysteine mutein" or "CTLA4 mutein," as used herein, refers to muteins having at least one cysteine that is not involved in an intramolecular or intermolecular disulfide bond. The free cysteine can appear at any amino acid residue that does not substantially interfere with its ability to bind B7.

The muteins and other derivatives can be prepared by methods well known to those skilled in the art. Such methods include, for example, mutagenic techniques in which nucleotides are substituted or added that encode for a cysteine. Alternatively, the muteins can be synthesized by methods also known to those skilled in the art.

In one embodiment, the cysteine mutein can be attached to polyethylene glycol (PEG) at a free cysteine to increase its molecular weight and improve its pharmacokinetic properties such as an increased serum half-life. Long chain polymer units of PEG can be bonded to the mutein via covalent attachment to the sulfhydryl group of a free cysteine residue on the mutein.

Various PEG polymers with different molecular weights can be used, for example, 5.0 kDa (PEGs), 8.5 kDa (PEGs), 10 kDa (PEGs) and 20 kDa (PEGs). To obtain selectivity of reaction and homogenous reaction mixture, it is useful to use functionalized polymer units that will react specifically with the sulfhydryl groups. The functional or reactive group attached to the long chain PEG polymer is the activating group to which the mutein attaches at the free cysteine site. Suitable activating groups include, for example, maleimide, sulfhydryl, thiol, triflate, tresylate, aziridine, exirane or 5-pyridyl. PEG molecules can also be attached to the protein of the invention at free amines using NHS(N-hydroxysuccinimide)-derivatized PEG molecules.

Other conjugates of the protein of the invention are also contemplated, for example, (1) by attaching a single PEG molecule to a monomer (monopegylated) or dimer, for example, at free amines; (2) by attaching two PEG molecules to a dimer of the protein of the invention. Those skilled in the art can readily determine the appropriate pH, concentration of polypeptide, and ratio of polypeptide to PEG necessary to produce a useful yield of the pegylated polypeptide.

The present invention further provides pharmaceutical compositions containing the protein of the invention or its functional derivatives in a pharmaceutically acceptable carrier.

The term "pharmaceutically acceptable carrier" as used herein means a non-toxic, generally inert vehicle for the active ingredient, which does not adversely affect the ingredient or the patient to whom the composition is administered. Suitable vehicles or carriers can be found in standard pharmaceutical texts, for example, in Reminston's Pharmaceutical Sciences, 16th ed., Mack Publishing Co., Easton, Pa. (1980), incorporated herein by reference. Such carriers include, for example, aqueous solutions such as bicarbonate buffers, phosphate buffers, Ringer's solution and physiological saline. In addition, the carrier can contain other pharmaceutically-acceptable excipients for modifying or maintaining the pH, osmolarity, viscosity, clarity, colour, sterility, stability, rate of dissolution, or odour of the formulation.

The pharmaceutical compositions can be prepared by methods known in the art, including, by way of an example, the simple mixing of reagents. Those skilled in the art will know that the choice of the pharmaceutical carrier and the appropriate preparation of the composition depend on the intended use and mode of administration.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form that requires reconstitution prior to administration.

Generally, storage of the formulations is at temperatures conventional for such pharmaceuticals, including room temperature or preferably 40° C. or lower, such as −70° C. The formulations can be stored and administered between a pH range of about 5 to 8, preferably at about physiological pH.

The recombinant polypeptides and functional derivatives thereof can be used to prevent, suppress or treat disorders associated with Inappropriate T cell activation and proliferation. Accordingly, the present Invention provides methods for the therapy of disorders associated with such deleterious T cell activation and proliferation. Such disorders include, for example, transplantation rejection, various autoimmune diseases and allergies and other T-cell mediated disorders. The autoimmune diseases for which the administration of the protein of the invention and functional derivatives may be useful include rheumatoid arthritis, asthma, lupus, multiple sclerosis, psoriasis, graft versus host disease, Type I diabetes and other autoimmune diseases.

The therapeutic methods of the present invention are accomplished by administering to a patient an effective amount of a protein of the invention or a functional derivative thereof to inhibit deleterious T cell activation. The active ingredient is preferably formulated into a pharmaceutical composition as previously described.

As used herein, the term "patient" refers to any human having T cells that are capable of being co-stimulated by B7. In addition, the protein of the invention and its functional derivative is also referred to as the "active ingredient(s)." An effective dosage depends on a variety of factors known to those skilled in the art, including the species, age, weight, and medical condition of the patient, as well as the type of disorder to be prevented, suppressed or treated, the severity of the condition, the route of administration and the active ingredient used. A skilled physician or veterinarian can readily determine and prescribe an effective amount of the active ingredient.

Generally, treatment is initiated with small dosages substantially less than the optimum dose of the active ingredient. Thereafter, the dosage is increased by small increments until the optimum or desired effect is attained without causing significant harm or deleterious side effects.

Preferably, the daily dosage is in the range of about 10-5000 mg per human patient.

The compounds and pharmaceutical compositions of the present invention can be administered orally or parenterally by any means known in the art, including, for example, by intravenous, subcutaneous, intraarticular or intramuscular injection or infusion. To achieve and maintain the desired effective dose, repeated administration may be desirable. The frequency of dosing will depend on several factors such as, for example, the formulation used, the type of disorder, the individual characteristics of the patient, and the like. Those skilled in the art can readily determine the appropriate frequency based on such factors.

The protein of the invention can also be used to contact a donor bone marrow with the protein of the invention and with cells from the transplant recipient ex vivo prior to transplantation of the donor bone marrow into the recipient. More specifically, antigen presenting cells of the recipient are incubated with the protein of the invention and are contacted with cells, most preferably T cells of the donor. Alloreactive T cells will be anergized, driven into apoptosis or educated to T regulatory cells this way.

EXAMPLES

The following examples are intended to illustrate but not limit the present invention.

Reduction of CD86 by hCtla4 in Raji Cells

FIG. 1: Raji cells (human B cell lymphoma) were infected with a vector coding for hCTLA4Ig or hCTLA4Cys (sCTLA4) (proteins of the invention). Surface expression of CD86 was analysed several times. This figure shows day 7 post infection. The transfection rate was not evaluated. It can clearly be seen, that the number of CD86 low Raji cells increased, when any of the CTLA4 constructs was expressed in the cell population. The sCTLA4 (Ctla4Cys) was more efficient (6,3%) then the Ctla4Ig (3,6%).

Reduction of CD86 by sCtla4 in A20 Cells

FIG. 2: Transfection of A20 cells (mouse B cell lymphoma) with sCTLA4 protein of the invention (Ctla4Cys) drastically reduces the surface amount of CD86. Increasing the sCTLA4 amount by a second transfection, reduces the CD86 amount even further. It is known that only the CTLA4 dimer efficiently binds CD86.

Reduction of CD86 by the Protein of the Invention in Primary Dendritic Cells

FIG. 3: Primary mDC were infected at day 3 after isolation with a MOI of 1 or 0.2 with virus coding for sCTLA4 (mCTLA4Cys). CD86 expression of these cells was measured frequently. The upper row shows mDC three days after infection (day 6 of culture). The lower row shows mDC eight days after infection. On day 7, 16 hours before the analysis, the cells were supplemented with 0.1 ng LPS/ml. The increase of the CD86 amount in the transfected cells was hampered by expression of sCTLA4 (Ctla4Cys).

The foregoing description of the invention is exemplary for purposes of illustration and explanation. It should be understood that various modifications can be made without departing from the spirit and scope of the invention.

Accordingly, the following claims are intended to be interpreted, to embrace all such modifications.

The invention claimed is:

1. An isolated protein of amino acid sequence (SEQ ID NO: 3)

Z¹mhvaqpavvlassrgiasfvceyaspgkatevrvtvlrqadsqvtevcaatymtgneltflddsic
tgtssgnqvnltiqglramdtglyickvelmypppyylgigngtqiyvidpepcpds-Z²
gtssgnqvnltiqglramdtglyickvelmypppyylgigngtqiyvidpepcpds-Z²
Z¹mhvaqpavvlassrgiasfvceyaspgkatevrvtvlrqadsqvtevcaatymtgneltflddsict wherein Z¹ is (i) a signal peptide for protein transport to the ER and/or through the plasma membrane, (ii) $NH_2$, (iii) an alkylated derivative of $NH_2$, (iv) an acylated derivative of $NH_2$, or (v) a polyethylene glycol (PEG) moiety and Z² is (i) an amino acid chain wherein the chain has up to 20 non-hydrophobic naturally occurring amino acids, or (ii) $COOZ^3$ wherein $Z^3$ is hydrogen or a metal ion.

2. The protein of claim 1 wherein the chain has 8 or 10 amino acids.

3. A monomeric protein (SEQ ID NO: 1)
Z¹-mhvaqpavvlassrgiasfvceyaspgkatevrvtvlrqadsqvtevc aatymtgneltflddsictgtssgnqvnltiqglramdtglyickvelmy pppyylgigngtqiyvidpepcpds-Z², of dimeric protein (SEQ ID NO: 3)

Z¹mhvaqpavvlassrgiasfvceyaspgkatevrvtvlrqadsqvtevcaatymtgneltflddsic
tgtssgnqvnltiqglramdtglyickvelmypppyylgigngtqiyvidpepcpds-Z²
gtssgnqvnltiqglramdtglyickvelmypppyylgigngtqiyvidpepcpds-Z²
Z¹mhvaqpavvlassrgiasfvceyaspgkatevrvtvlrqadsqvtevcaatymtgneltflddsict, wherein Z¹ is (i) a signal peptide for protein transport to the ER and/or through the plasma membrane, (ii) $NH_2$, (iii) an alkylated derivative of $NH_2$, (iv) an acylated derivative of $NH_2$, or (v) a polyethylene glycol (PEG) moiety and Z² is (i) an amino acid chain wherein the chain has up to 20 non-hydrophobic naturally occurring amino acids, or (ii) $COOZ^3$ wherein $Z^3$ is hydrogen or a metal ion.

4. The protein of claim 1 wherein $Z^1$ is (SEQ ID NO: 2)
maclgfqrhk aqlnlaartw pctllfflllf ipvfcka.

5. The protein of claim 1 which is soluble under physiological conditions.

6. The protein of claim 1 comprising an extracellular domain of the CTLA4 protein.

7. The protein of claim 1 binding B7-1 or B7-2.

8. The protein of claim 3 crosslinked to PEG-moieties.

9. A composition suitable for pharmaceutical administration comprising the protein of claim 1 and a pharmaceutically acceptable carrier.

10. A composition suitable for pharmaceutical administration comprising the monomeric protein of claim 1 and a pharmaceutically acceptable carrier.

* * * * *